(12) United States Patent
Adachi et al.

(10) Patent No.: US 7,001,885 B2
(45) Date of Patent: Feb. 21, 2006

(54) METHOD FOR REMOVING MULTIMERS OF HUMAN SERUM ALBUMIN

(75) Inventors: Satoshi Adachi, Kumamoto (JP); Hiroshi Mizokami, Kumamoto (JP); Yoshitaka Tajima, Kumamoto (JP); Yoshinobu Miyatsu, Kumamoto (JP); Toshinobu Nouchi, Kumamoto (JP); Yoshitaka Ushio, Kumamoto (JP)

(73) Assignee: Juridical Foundation the Chemo-Sero-Therapeutic Research Institute, Kumamoto (JP)

( * ) Notice: Subject to any disclaimer, the term of this patent is extended or adjusted under 35 U.S.C. 154(b) by 0 days.

(21) Appl. No.: 10/175,382

(22) Filed: Jun. 20, 2002

(65) Prior Publication Data

US 2002/0183492 A1   Dec. 5, 2002

Related U.S. Application Data

(63) Continuation of application No. PCT/JP01/09335, filed on Oct. 24, 2001.

(30) Foreign Application Priority Data

Oct. 24, 2000   (JP) ............................ 2000-324029

(51) Int. Cl.
*A61K 38/00* (2006.01)
(52) U.S. Cl. ........................................ 514/12
(58) Field of Classification Search ............... 530/350, 530/364, 402; 514/2, 12; 435/7, 69.1, 69.6, 435/71
See application file for complete search history.

(56) References Cited

U.S. PATENT DOCUMENTS

| 4,169,829 A | | 10/1979 | Plan et al. | |
| 4,705,848 A | | 11/1987 | Yang et al. | |
| 5,132,404 A | * | 7/1992 | Ohtani et al. | 530/364 |
| 5,710,253 A | * | 1/1998 | Ohtani et al. | 530/364 |
| 5,728,553 A | | 3/1998 | Goodey et al. | |
| 5,986,062 A | * | 11/1999 | Ohmura et al. | 530/363 |

FOREIGN PATENT DOCUMENTS

| EP | 0 073 646 A2 | 9/1983 |
| EP | 0 319 067 | 7/1989 |
| EP | 0 367 220 | 5/1990 |
| EP | 0 570 916 A2 | 11/1993 |
| JP | 02-111728 | 4/1990 |
| JP | 3-17023 | 1/1991 |
| JP | 03-103188 | 4/1991 |
| JP | 06-71434 | 9/1994 |
| JP | 07-126182 | 5/1995 |
| JP | 08-116985 | 5/1996 |
| JP | 29-26722 | 5/1999 |
| JP | 11-509525 | 8/1999 |
| WO | WO 99/62936 | 12/1999 |

OTHER PUBLICATIONS

Ion Exchange Chromatography, Pharmacia Fine Chemicals, (Mar. 1, 1980). Technical manual, printed in Sweden by Rahm I Lund.*
Alan V. Quirk et al., *Production of Recombinant Human Serum Albumin from Saccharomyces cerevisiae*, Biotechnology and Applied Biochemistry, 11, 273-287 (1989).
Ken Okabayashi et al., *Secretory Expression of the Human Serum Albumin Gene in the Yeast Saccharomyces cerevisiae*, J. Biochem., 110, 103-110 (1991).
Richard G. Buckholz et al., *Yeast Systems for the Commercial Production of Heterologous Proteins*, Biotechnology, vol. 9, Nov. 1991, pp. 1067-1072.
Martine Latta et al., *Synthesis and Purification of Mature Human Serum Albumin from E. coli*, Biotechnology, vol. 5, Dec. 1987, pp. 1309-1314.
Charles W. Saunders, et al., *Secretion of Human Serum Albumin from Bacillus subtilis*, Journal of Bacteriology, vol. 169, No. 7, Jul. 1987, p. 2917-2925.
Phillip P. Minghetti et al., *Molecular Structure of the Human Albumin Gene is Revealed by Nucleotide Sequence Within q11-22 of Chromosome 4*, The Journal of Biological Chemistry, vol. 261, No. 15, May 25, 1986, pp. 6747-6757.
Jan H. Bergloef et al., *Chromatographic Preparation and in Vitro Properties of Albumin from Human Plasma*, Journal of Applied Biochemistry, vol. 5, 282-292 (1983).
U.S. Appl. No. 10/175,103, filed Jun. 20, 2002, pending.
U.S. Appl. No. 10/175,781, filed Jun. 21, 2002, pending.
U.S. Appl. No. 10/175,382, filed Jun. 20, 2002, pending.

* cited by examiner

*Primary Examiner*—Jon Weber
*Assistant Examiner*—Agnes Rooke
(74) *Attorney, Agent, or Firm*—Oblon, Spivak, McClelland, Maier & Neustadt, P.C.

(57) ABSTRACT

Multimers of human serum albumin are removed from a solution of human serum albumin containing the multimers by bringing the human serum albumin solution into contact with an anion-exchanger equilibrated with a buffer containing a salt in a concentration ranging from 10 to 150 mM and having a pH value ranging from 5 to 9.5.

8 Claims, 1 Drawing Sheet

METHOD FOR REMOVING MULTIMERS OF HUMAN SERUM ALBUMIN

This application is a continuation of PCT/JP01/09335 filed on Oct. 24, 2001, and claims priority to JAPAN 2000-324029 filed on Oct. 24, 2000.

TECHNICAL FIELD

The present invention relates to a method for removing a multimer of human serum albumin. More specifically, the present invention pertains to a method for removing a multimer of human serum albumin, which comprises the step of bringing a human serum albumin solution containing multimers of human serum albumin into contact with an anion-exchanger under specific conditions.

BACKGROUND ART

Human serum albumin (hereunder also referred to as "HSA") is a principal protein component present in the plasma, consists of a single chain polypeptide comprising 585 amino acid residues and has a molecular weight equal to about 66,000 Dalton (see Minghetti, P. P. et al. (1986), Molecular structure of the human albumin gene is revealed by nucleotide sequence within 11–22 of chromosome 4. J. Biol. Chem. 261, pp. 6747–6757). It has been known that the principal roles of HSA are not only to maintain the normal osmotic pressure of the blood, but also to bind with a variety of substances such as calcium ions, fatty acids, bilirubin, tryptophan and drugs possibly present in the blood, thereby playing a role of a carrier for transporting these substances. Purified HSA has been used in, for instance, the postoperative treatment after surgical operations and the treatment of hypoalbuminemia caused due to the loss of albumin such as hemorrhagic shock, burn and nephrotic syndromes.

Conventionally, HSA has been prepared by subjecting the human plasma to the low temperature ethanol-fractionation method of Cone or any method similar thereto to give HSA-containing fractions (HSA is fractionated in the fraction V) and then purifying the fraction through the use of a variety of purification techniques. Moreover, there has recently been developed a method in which the human plasma is not used as a raw material, for instance, a technique for producing human serum albumin using yeast, Escherichia coli or Bacillus subtilis cells, while making use of the gene recombination technique.

These gene recombination techniques are detailed in (1) Production of recombinant Human Serum Albumin from Saccharomyces cerevisiae; Quirk, R. et al. Biotechnology and Applied Biochemistry, 1989, 11: 273–287, (2) Secretory Expression of the Human Serum Albumin Gene in the Yeast, Saccharomyces cerevisiae; Ken Okabayashi et al. J. Biochemistry, 1991, 110: 103–110, (3) Yeast Systems for the Commercial Production of Heterologous Proteins; Richard G. Buckholz and Martin A. G. Gleeson, Bio/Technology, 1991, 9: 1067–1072 for the yeast, (4) Construction of DNA sequences and their use for microbial production of proteins, in particular, human serum albumin; Lawn, R. M. European Patent Publication No. 0073646A (1983), (5) Synthesis and Purification of mature human serum albumin from E. coli; Latta, L. et al. Biotechnique, 1897, 5: 1309–1314 for the Escherichia coli (E. coli), (6) Secretion of human serum albumin from Bacillus subtilis; Saunders, C. W. et al. J. Bacteriol. 1987, 169: 2917–2925 for the Bacillus subtilis.

The methods for purifying the human serum albumin usable herein in general include those currently used in the protein chemistry such as a salting out method, an ultrafiltration method, an isoelectric precipitation method, an electrophoresis method, an ion-exchange chromatography technique, a gel filtration chromatography technique and/or an affinity chromatography technique. Indeed, the human serum albumin-containing fraction includes various kinds of contaminants originated from, for instance, biological tissues, cells and blood and therefore, the human serum albumin has been purified by a complicated combination of the foregoing methods.

In the industrial production of human serum albumin, it is inevitable to treat the same under various conditions different from environmental conditions observed in the human body and accordingly, multimers of human serum albumin are formed. There has not yet been known any such a report that these multimers adversely affect the human body in the clinical application of human serum albumin, but there is such a suspicion that these multimers may develop a novel antigenicity. For this reason, an upper limit in the contamination with these multimers is prescribed in the standardization test of "human serum albumin" as a pharmaceutical agent from the viewpoint of the safety thereof as a medicine and therefore, it becomes an important problem, in the production of a pharmaceutical preparation containing the same, to substantially reduce the content of such multimers in the preparation.

Two or more molecules of human serum albumin are linked with one another to form such a multimer thereof, the isoelectric point and chemical characteristics of the latter are correspondingly quite similar to those observed for the monomer and therefore, it is very difficult to separate the multimers from the monomers according to the purification methods employed in the usual production process. For this reason, the multimers have been removed, in the conventional techniques, by a combination of several kinds of purification methods selected from the group consisting of gel filtration chromatography, ion-exchange chromatography, affinity chromatography, isoelectric fractionation, ammonium sulfate fractionation and ethanol fractionation techniques (see, TOKUHYO Hei 11-509525 (International Patent Publication WO96/37515) and Japanese Patent No. 2,926,722 (registered on Heisei 11 (1999), May 14)).

If a plurality of purification methods is used in combination, the final rate of recovery is the product of those achieved in the purification steps used and therefore, the resulting productivity is significantly reduced in most cases. Accordingly, there has been desired for the development of a method, which can reduce the number of purification steps as low as possible, permits the effective removal of multimers of human serum albumin and allows the recovery of monomers thereof at a high yield, from the industrial standpoint.

DISCLOSURE OF THE INVENTION

Accordingly, it is an object of the present invention to provide a single-stage method for efficiently removing the multimers of human serum albumin formed during the process for preparing the human serum albumin.

It is another object of the present invention to provide human serum albumin having a high safety as a medicine.

According to an aspect of the present invention, there is provided a method for removing a multimer of human serum albumin, wherein a human serum albumin solution containing the multimer is brought into contact with an anion-exchanger equilibrated with a buffer containing a salt in a concentration ranging from 10 to 150 mM and having a pH value ranging from 5 to 9.5. According to another aspect of the present invention, there is provided high purity human serum albumin, which is prepared by a production process including the step of the foregoing method and whose multimer content is reduced. The present invention will hereunder be described in more detail.

BEST MODE FOR CARRYING OUT THE INVENTION

Figure 1:
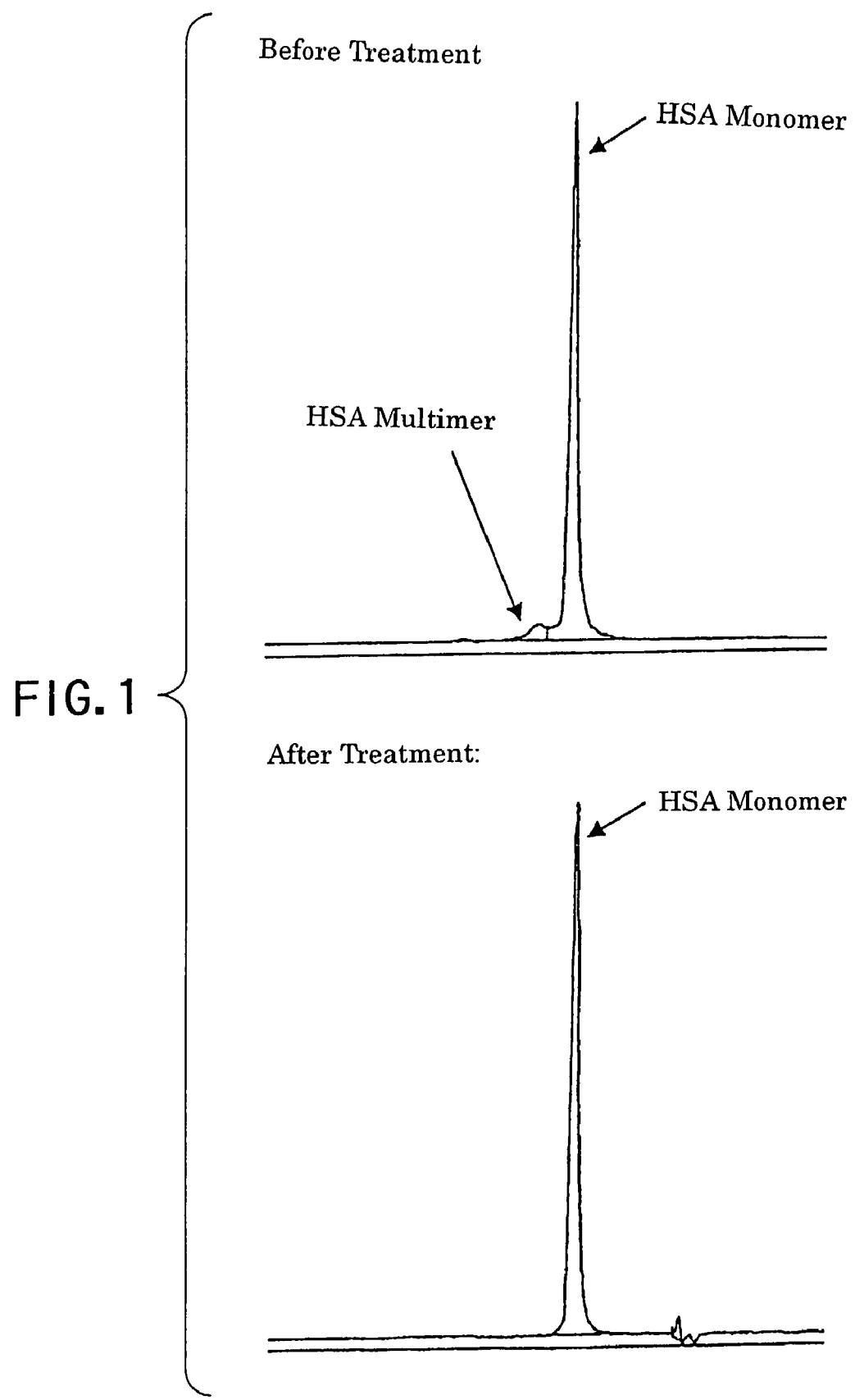
FIG. 1 is a diagram showing the results obtained by subjecting, to the gel filtration HPLC, a sample obtained after dialyzing a solution of HSA containing multimers thereof against a 50 mM phosphate buffer (pH 6.5) containing 75 mM NaCl (sample before a treatment) and a fraction obtained by treating the dialyzed sample with a strong anion-exchange chromatography column equilibrated with the same buffer solution and collecting a fraction passing through the same (sample after the treatment).

The method of the present invention is characterized by treating a human serum albumin solution containing a multimer thereof with a buffer solution having an appropriate salt concentration, subsequently bringing the human serum albumin solution into contact with an anion-exchanger equilibrated with the same buffer solution to thus adsorb the multimer on the anion-exchanger thereby removing the multimer from the human serum albumin solution and then recovering the resulting high purity human serum albumin. Thus, the method of the present invention would permit the efficient preparation of high purity human serum albumin substantially free of any multimer of human serum albumin.

The human serum albumin to be subjected to the foregoing treatment with an anion-exchanger may be recombinant human serum albumin obtained through the gene recombination technique (hereunder also referred to as "rHSA") or HSA.

When preparing HSA from the plasma, it would be predicted that the multimer might be formed in each step, but aqueous multimer-containing solutions obtained in any such step may be used in the invention. Examples of such aqueous solution are an aqueous solution of the fraction V obtained through the low temperature alcohol-fractionation and multimer-containing aqueous solutions generated in the subsequent various purification steps (such as chromatography and heat-treatment) of the fraction V.

The multimer-containing aqueous solutions generated in the various steps for preparing rHSA can likewise be used in the present invention. Specific examples thereof are culture broth of rHSA-producing host cells and multimer-containing aqueous solutions generated in the subsequent various purification steps (such as chromatography and heat-treatment) for the culture broth. In this respect, the term "culture broth" used herein includes the culture broth in which the foregoing host cells are cultivated, and crushed host cell-containing liquids wherein the host cells are crushed by any currently used method.

The rHSA-producing host is not restricted to any specific one and those usable herein include, for instance, yeast, *Escherichia coli, Bacillus subtilis* and animal cells. Preferably used herein are yeast cells such as those belonging to the genus *Saccharomyces* and *Pichia*, with *Saccharomyces cerevisiae* AH22 strain or mutants thereof being more preferred.

In the method of the present invention, it is desirable to use a human serum albumin containing contaminants originated from the plasma or the recombinant host cells, which is purified to some extent (purity of HSA or rHSA of not less than about 85%) by processing steps such as ultrafiltration, heat-treatment, ion-exchange chromatography, adsorption chromatography, gel filtration chromatography and/or salting out techniques.

The kinds of buffer solutions used for preparing the foregoing albumin solution are not restricted to specific ones, but preferably used herein include, for instance, phosphate buffer solutions and Tris-HCl buffer solutions used in the usual anion-exchange chromatography. The concentration of buffering components present in the buffer solution is in general set at a level currently used in the usual anion-exchange chromatography. More specifically, the concentration thereof preferably ranges from 5 to 200 mM and more preferably 10 to 100 mM.

It is sufficient in the present invention to adjust the pH value of the buffer solution to the range within which the multimer of human serum albumin can be adsorbed on the anion-exchanger in the buffer solution free of any salt. More specifically, the pH value of the buffer solution used herein ranges from 5 to 9.5, preferably 5.5 to 7.5 and more preferably 6 to 7.

Examples of salts added to the buffer solution include alkali metal chlorides such as sodium chloride and potassium chloride, with sodium chloride being preferably used herein. The concentration of the salt is preferably selected in such a manner that the multimer can be adsorbed on the anion-exchanger, but any monomer is never adsorbed thereon. It is appropriately adjusted depending on the kind, concentration and pH value of the buffer solution used and may be in the range of from 10 to 150 mM, preferably 25 to 100 mM and more preferably 50 to 75 mM.

A solution of human serum albumin multimer-containing human serum albumin dissolved in a buffer solution having a salt concentration ranging from 10 to 150 mM and a pH value ranging from 5 to 9.5 may be prepared using, for instance, a method comprising the step of substituting the medium of the human serum albumin solution with the buffer solution through dialysis of a human serum albumin dissolved in an arbitrary solution against a buffer solution having a salt concentration ranging from 10 to 150 mM and a pH value ranging from 5 to 9.5; a gel filtration method; or a method comprising the steps of once concentrating a human serum albumin solution, diluting the concentrated albumin solution with the foregoing buffer and then repeating these two steps over desired times to thus substitute the medium of the initial albumin solution with the buffer.

The concentration of human serum albumin in the solution thereof is not restricted to any specific one insofar as the human serum albumin is completely dissolved in the solution and it preferably ranges from 1 to 30% and more preferably 5 to 25%.

As to the basic carrier for the anion-exchanger, it is preferred to select one, which never non-specifically adsorbs the human serum albumin. In addition, the anion-exchange groups usable herein may be either strong anion-exchange or weak anion-exchange groups, but the former is preferably used in the invention. Such a strong anion-exchanger carrying strong anion-exchange groups is not restricted to any particular one and specific examples thereof include Q-Sepharose FF (available from Amersham-Pharmacia-Biotech Company) and Cellufine Q (available from Millipore Company).

Examples of methods for removing multimers of human serum albumin using an anion-exchanger include a method comprising the steps of treating an albumin solution containing a multimer of albumin by column chromatography to thus selectively adsorb the albumin multimer on the anion-exchanger and then recovering a fraction free of any multimer, which can pass through the column without being adsorbed thereon; and a method comprising the steps of batchwise bringing the multimer-containing albumin solution into contact with an anion-exchanger to thus selectively adsorb the multimer on the anion-exchanger, allowing the solution containing the anion-exchanger to stand or centrifuging the solution to thus separate the anion-exchanger from the solution and then recovering the resulting supernatant. In the present invention, either of these methods can be used. In case of column chromatography, for instance, conditions for the chromatography such as the column size and flow rate can appropriately be adjusted depending on the concentration and volume of a specific sample. For instance, the following column chromatography conditions are used for the treatment of 10 L of a 10% human serum albumin solution: a volume of the anion-exchanger of 25 L, a column size of 700 cm$^2$×35 cm and a flow rate of 1200 ml/min.

The extent of the removal of the human serum albumin multimer can be monitored by the analysis of a part of the liquid recovered during the treatment using the gel filtration high performance liquid chromatography (HPLC) technique. For instance, this analysis may be carried out by loading the sample solution onto a column, TSKgel G3000SW (available from Tosoh Corporation), eluting with 0.1M KH$_2$PO$_4$/0.3M NaCl buffer and then determining the absorbance of the resulting fractions at 280 nm.

EXAMPLES

Preparation Example

Preparation of a Solution of Multimer-Containing Human Serum Albumin

According to the method disclosed in TOKUHYO Hei 11-509525, rHSA was produced using yeast cells (*Saccharomyces cerevisiae*). This rHSA-containing culture broth was diluted with purified water to a total volume of about two times that of the original one and then the pH value of the diluted solution was adjusted to 4.5 using an aqueous acetic acid solution. Then the solution was loaded onto STREAMLINE SP Column (available from Amersham Pharmacia Biotech Company; diameter 60 cm×16 cm), which had been equilibrated with a 50 mM sodium acetate buffer solution (pH 4.5) containing 50 mM sodium chloride. Thereafter, the column was washed with a buffer solution identical to that used for equilibrating the column, followed by passing, through the column, a 50 mM phosphate buffer solution (pH 9.0) containing 300 mM sodium chloride to give rHSA-containing fractions. The pH value of the HSA-containing fraction eluted from the STREAMLINE SP Column was adjusted to 9.0 with a borate and then the fraction was allowed to stand over 5 hours to thus partially convert the multimer of human serum albumin into the monomers thereof.

Example 1

Strong Anion-Exchange Chromatography Subsequent to Dialysis

A human serum albumin solution containing 6.1% (determined by the gel filtration HPLC analysis) of the human serum albumin multimers prepared according to the same method used in Preparation Example was dialyzed against a 50 mM sodium phosphate buffer (pH 6.5) containing 50, 75 or 100 mM sodium chloride at room temperature for 8 hours, the dialyzed solution of human serum albumin was loaded onto Q-Sepharose FF Column (diameter 2.5 cm×10 cm), which had been equilibrated with the same buffer solution in advance, the same buffer solution was fed to the column (500 ml, rate of elution: 12 ml/min) and all of the fractions passed through the column without undergoing adsorption on the column were recovered.

Test Example 1

Gel Filtration HPLC Analysis

The fraction (0.02 ml) passed through the column without undergoing adsorption and obtained in Example 1 was loaded onto TSKgel G3000SW (available from Tosoh Corporation) (diameter 0.75 cm×30 cm), which had been equilibrated with a 0.1 M KH$_2$PO$_4$ buffer containing 0.3 M NaCl and the gel filtration HPLC analysis was conducted at a detection wavelength of 280 nm. The results thus obtained in this Text Example 1 are summarized in the following Table 1 and plotted on FIG. 1.

TABLE 1

| Sample | Rate of Recovery of rHSA (%) | Monomer Content (%) | Multimer Content (%) |
|---|---|---|---|
| Sample Before the Treatment | | 93.9 | 6.1 |
| Sample Treated with Buffer Containing 50 mM NaCl | 98.3 | 100.0 | 0.0 |
| Sample Treated with Buffer Containing 75 mM NaCl | 97.2 | 100.0 | 0.0 |
| Sample Treated with Buffer Containing 100 mM NaCl | 98.5 | 98.1 | 1.9 |

The data listed in Table 1 indicate that human serum albumin whose multimer concentration is reduced can be obtained at a high yield, when a multimer-containing human serum albumin solution is dialyzed against a phosphate buffer solution containing sodium chloride in a concentration ranging from 50 to 75 mM and then the dialyzed solution is passed through a strong anion-exchange column equilibrated with the same buffer solution used above to thus selectively adsorb the multimer on the strong anion-exchanger.

INDUSTRIAL APPLICABILITY

The present invention permits the efficient removal of multimers of human serum albumin and the recovery of monomers of human serum albumin at a high yield by substituting the medium. of a solution of human serum albumin containing multimers thereof with a buffer solution having a desired composition and then bringing the buffered solution into contact with an anion-exchanger equilibrated with the same buffer solution.

In addition, the method of the present invention also permits the preparation of high purity human serum albumin substantially free of any multimer of human serum albumin, which may become a cause of side effects such as shock or allergy observed when it is administered to the human.

What is claimed is:

1. A method for purifying a recombinant human serum albumin monomer from its multimers, comprising:
   (1) treating a recombinant human serum albumin solution at pH 9.0 to convert the multimers of recombinant human serum albumin into monomers, and
   (2) loading treated recombinant human serum albumin solution onto an anion-exchange column equilibrated with a buffer with a concentration range from 5 to 200 mM containing added salt concentration ranging from 50 to 100 mM an having a pH value from 6.0 to 7.0 and recovering all of the fractions passed through the column without undergoing absorption.

2. The method of claim 1, wherein the salt concentration in the buffer in (2) ranges from 50 to 75 mM.

3. The method of claim 1, wherein the purity of the recombinant human serum albumin in the recombinant human serum albumin solution to be treated is not less than about 85%.

4. The method of claim 2, wherein the purity of the recombinant human serum albumin in the recombinant human serum albumin solution to be treated is not less than about 85%.

5. The method of claim 2, wherein the salt is an alkali metal chloride.

6. The method of claim 2, wherein the salt is sodium chloride.

7. The method of claim 2, wherein the salt is potassium chloride.

8. The method of claim 1 wherein the buffer has a concentration range of 10–100 mM.

* * * * *